United States Patent [19]

Urabe et al.

[11] Patent Number: 5,378,687

[45] Date of Patent: Jan. 3, 1995

[54] USE OF HUMAN BLOOD COAGULATION FACTOR XIII FOR THE TREATMENT OF ULCERATIVE COLITIS

[75] Inventors: Mikio Urabe, Fukuoka; Satoshi Tanaka, Chiba; Kenichiro Tsumura, Ichihara, all of Japan

[73] Assignee: Hoechst Japan Limited, Tokyo, Japan

[21] Appl. No.: 60,702

[22] Filed: May 13, 1993

Related U.S. Application Data

[63] Continuation of Ser. No. 839,080, Feb. 24, 1992, abandoned, which is a continuation of Ser. No. 704,737, May 20, 1991, abandoned, which is a continuation of Ser. No. 152,822, Feb. 5, 1988, abandoned.

[30] Foreign Application Priority Data

Feb. 9, 1987 [JP] Japan .................................. 62-26387

[51] Int. Cl.$^6$ .................... A61K 37/00; A61K 37/48
[52] U.S. Cl. .............................. 514/12; 514/21; 530/381; 530/384; 424/94.1
[58] Field of Search .................... 514/12, 21; 530/381, 530/384; 424/94.1

[56] References Cited

PUBLICATIONS

Knot E., Ten Cate J. W., Leeksma Och, Tytgat G. N., Vreenken J (1983) No Evidence for a Prethrombotic State in Stable Chronic Inflammatory Bowel Disease. J Clin Pathol 36: 1387–1390.
Klingemann H.-G., Egbring, R. Holst F., Gramse M. Havemann K. (1982) Degradation of Human Plasma Fibrin Stabilizing Factor XIII Subunits by Human Granulocytic Proteinases. Thromb Res 28: 793–801.
Trobisch H., Egbring R. (1972) Substitution mit Einem Neuen Faktor-XIII-Konzentrat Bei Kongenitalem Faktor-XIII-Mangel. Dtsch Med Wschr 97: 499–502.
Britten AFH (1967) Congenital Deficiency of Factor XIII (Fibrin-Stabilizing Factor). Report of a Case and Review of the Literature. Am J Med 43: 751–760.
Rodeghiero F., Castaman G. C., Di Bona E., Ruggeri M., Dini E. (1987) Successful Pregnancy in a Woman with Congential Factor XII Deficiency Treated with Substitutive Therapy. Report of a Second Case. Blut 55: 45–48.
Suzuki H., Kaneda T. (1985) Tooth Extraction in Two Patients Who Had a Congential Deficiency of Factor XIII. J Oral Maxillofac Surg 43: 221–224.
Kuratsuji T. Oikawa T., Fukumoto T., Shimizu S., Iwasaki Y., Tomita Y., Meguro T., Yamada K. (1982) Factor XIII Deficiency in Antibiotic-Associated Pseudomembranous Colitis and its Treatment with Factor XIII Concentrate. Haemostasis 11: 229–234.
Kuratsuji et al. (1982) Haemostasis 11, 229–234.
Suzuki et al (1987) Jpn. J. Gastroenterology 84(2), 127.
Suzuki & Takamura "Coagulation Findings in Ulcerative Colitis . . . " Biosis 88: 21341 Jul. 1987.
Kuratsuji, et al "Factor XIII Deficiency in Antibiotic-Associated . . . " Haemostasis 11: 229–234, 1982.
Suzuki et al "Blood Coagulation Factors in Ulcerative Colitis . . . " Japanese J. Gastroenterology v. 84(2) p. 127 Feb. 1987.

*Primary Examiner*—Keith Baker
*Attorney, Agent, or Firm*—Finnegan, Henderson, Farabow, Garrett & Dunner

[57] ABSTRACT

Use of human blood coagulation factor XIII for the treatment of ulceration colitis The use of human blood coagulation factor XIII for the treatment of ulcerative colitis is demonstrated in 4 representative cases. Treatment with factor XIII leads to rapid and total disappearence of the chief symptoms realizing transition to the remission stage.

4 Claims, No Drawings

USE OF HUMAN BLOOD COAGULATION FACTOR XIII FOR THE TREATMENT OF ULCERATIVE COLITIS

This application is a continuation of application Ser. No. 07/839,080, filed Feb. 24, 1992, now abandoned, which is a continuation of Ser. No. 07/704,737, filed May 20, 1991, abandoned, which is a continuation of Ser. No. 07/152,822 filed Feb. 5, 1988, abandoned.

This invention relates to the use of human blood coagulation factor XIII for the treatment of ulcerative colitis.

Ulcerative colitis is designated as a specified disease and is defined as erosive non-specific inflammation of the colon that mainly affects the intestinal mucosa and often causes erosion or ulceration. It usually develops bloody diarrhea and a variety of systemic symptoms. With regard to its etiology, there are may hypotheses, including those asserting the association of infection, bacterial allergy, enzyme and psychoneurosis. In recent years, however, emphasis has been placed on the possible association of prostaglandins and immune disorders.

Immunosuppressive therapy, or administration of anti-immune agents, such as 6-mercaptopurine, has been attempted as a specific treatment for ulcerative colitis, considering that immune disorders are one of the possible causes of the disease. This therapy, however, has failed to work as a radical therapeutic means. At present, this disease is being treated only with symptomatic methods, such as the oral, intravenous, topical and intraintestinal administration of anti-inflammatory agents, such as steroid hormones.

None of the existing therapeutic methods are able to attain prompt, complete disappearance of the chief gastrointestinal symptoms (e.g., diarrhea, bloody stools, abdominal pain) in the active stage of this disease. Nor can they produce sufficient effect for quick transition from the active stage to the remission stage.

A therapy in accordance with this invention makes it possible to achieve total disappearance of the chief symptoms in a short period of several days and to realize quicker transition to the remission stage.

This invention relates to a pharmaceutical composition for treatment of ulcerative colitis, which contains human blood coagulation factor XIII (hereinafter referred to as factor XIII) as the active ingredient.

Factor XIII preparations have been used mainly to treat wound healing disturbances. We, the inventors of this invention, have found factor XIII to cure ulcerative colitis. This finding has led us to accomplish the invention.

The existence of factor XIII was first suggested by Robbins in 1944. In the early days it had also been called fibrin-stabilizing factor, fibrinase or plasma transglutaminase, but, after studies by Laki end Lorand et el., factor XIII was adopted as its official name at the Congress of the International Society on Thrombosis and Haemostasis in 1963. It is commonly seen in the plasma, placenta. etc. It acts as a transaminase that is activated by thrombin and $Ca^{2+}$ and forms cross-bridges between fibrin molecules. Those cross-bridges grow into a strong fibrin network that is tolerable against physical shocks and chemical stimuli. Besides this fibrin-stabilizing effect, factor XIII has also been demonstrated to play an important role in the wound healing process: that is, it forms cross-bridges between fibrin and fibronectin molecules and promotes fibroblast proliferation and epidermis formation.

Factor XIII preparations have already been in wide use as a therapeutic agent for wound healing disturbances, etc. The number of domestic and overseas patients treated with them has exceeded 10,000. This accumulation of clinical experience ensures that they are totally free from side effects and toxicity as long as they are used at a usual dose of 20 to 50 units/kg body weight.

The following are the detailed results of clinical trials that clearly demonstrate the effectiveness of factor XIII in the treatment of ulcerative colitis, Case 1 (female, 35 years old, 43.0 kg): This patient experienced mucosanguineous stools and abdominal pain for the first time in January 1983. In January 1984 these symptoms recurred at a frequency of several times a day, and the diagnosis of total ulcerative colitis was made on the basis of x-ray and colonoscopic findings.

Treatment with 30 g salazosulfapyridine was immediately started. However, since the patient developed allergic symptoms, the drug was replaced by an antidiarrhetic, digestive, etc. and her condition was continuously observed. In December of the same year, blood was detected again in the stool and Predonine was administered at a dose of 15 mg per day. Thereafter the patient showed a good clinical course until January 1986, when she experienced mucosanguineous stools and abdominal pain again. The dosage of Predonine was increased to 40 mg per day, but this was not effective for either symptom. Therefore, a factor XIII concentrate in accordance with this invention was intravenously administered on trial at a daily dose of 2000 units for 3 days. Macroscopic mucus and blood in the stool and abdominal pain began to be alleviated on the day after the final administration and completely disappeared in the 2nd post-treatment week. Pulse rate and body temperature also began to return to normal shortly after treatment and were completely normalized one week after the final administration.

Case 2 (male, 31 years old, 37.5 kg), Around May 1984 this patient started to experience bloody stools and received the diagnosis of left-sided ulcerative colitis. Treated with Predonine at an intra-arterial dose of 60 mg and hydrocortisone at an intra-intestinal dose of 300 mg daily, his disease once remitted around April 1986. Thereafter his condition was kept under observation with salazosulfapyridine given at a maintenance dose of 40 g. In July of the same year, however, loose stools with a frequency of 5 or 6 times a day and abdominal pain occurred, with macroscopic findings of mucus and blood in the stools. Colonoscopic examination revealed erosion and contact bleeding in the rectum and mild edema in the rectal mucosa.

The factor XIII concentrate was intravenously administered at a daily dose of 2000 units for 3 consecutive days. Abdominal pain began to become milder during the treatment period and was completely removed on the day after the final administration. The defecating frequency decreased, and the macroscopic appearance of stools changed from the pretreatment mucous one to a normal one. No blood was detected in the stool on day 4 after treatment. The colonoscopic examination performed on the 14th post-treatment day demonstrated that edema and erosion had disappeared and that the images of blood vessels had become visible, indicating marked improvement.

Case 3 (female, 52 years old, 50 kg), This patient started to complain of diarrheal tendency, abdominal distention and dull abdominal pain in late August 1986. Left-sided ulcerative colitis was diagnosed in October of the same year on the basis of x-ray and colonoscopic findings. The colonoscopy at that time revealed the disappearance of seen-through blood vessel images in the recto-sigmoid region, the presence of erosive mucosal edema, redness and bleeding, and the formation of shallow, irregular-form, small ulcers, indicating that the disease was in the active stage.

The patient was prohibited from taking food, and intravenous hyperalimentation was performed. The factor XIII concentrate was intravenously administered for 3 days, at a daily dose of 1500 units. Bloody stools, bleeding following defecation, and abdominal distention began to be alleviated during this treatment period. The appearance of stools also improved. No blood was detected in the stool on the day following the 3-day treatment. However, the patient experienced abdominal pain and bloody stools again on the 4th post-treatment day. Intravenous administration of the factor XIII concentrate, 1500 units per day, was therefore performed again for 2 days. This led to removal of abdominal pain and other abdominal symptoms on the 4th post-treatment day and to detection of no blood in the stool and normalization of stool's appearance on the 5th post-treatment day. The colonoscopic examination performed 4 days after the first series of treatment demonstrated that mucosal damages were localized in the middle part of the sigmoid colon and below, that spontaneous bleeding was seen only in limited areas although contact bleeding due to suction was noted at some regions, and that the visibility of blood vessels had been remarkably improved. These colonoscopic findings revealed distinct improvement compared with the pretreatment findings, indicating that the patient was in the curing process although there was a recurrence of clinical symptoms.

Case 4 (male, 54 years old, 68 kg): This patient had been showing diarrheal tendency. A colonoscopic examination in November 1986 revealed disorders in the mucosal structure extending to the transverse colon as well as pseudopolyp-like elevations, bleeding and redness spreading all over the sigmoid colon. Ulcerative colitis being suspected, the factor XIII concentrate was intravenously administered at the daily dose of 2000 units for 3 days. Bloody diarrhea and abdominal pain started to be alleviated on the 2nd treatment day and were completely extinguished on day 3 following the final treatment. The colonoscopic examination performed i week after the final administration revealed that mucosal spasms extending to the sigmoid colon and bleeding had stopped, although a small number of pseudopolyps were still present.

PROCESS FOR PRODUCING FACTOR XIII CONCENTRATE

Factor XIII preparations are manufactured from human placenta or plasma by well-known methods. An example of the manufacturing methods using human placenta as raw material is as follows:

Freeze placentae and break them into fine pieces. Add an NaCl solution to the fine pieces of placentae, stir, and centrifuge to collect supernatant I. After ascertaining by enzyme immunoassay that this supernatant I is free from HBs antigen, add a Rivanol solution to it and collect precipitate II that contains factor XIII. After washing the precipitate, add an NaCl solution containing EDTA to it and stir. Remove undissolved substances (precipitate III) and obtain supernatant III. Then add an N-cetyl-pyridinium chloride solution to supernatant III to precipitate contaminating proteins and muco-polysaccharides. Add a Rivanol solution to the supernatant IV so obtained, and generate precipitate V that contains factor XIII. Add an Nacl solution containing EDTA to this precipitate V, stir, and remove undissolved substances (precipitate VI) to obtain supernatant VI. Add ammonium sulfate to supernatant VI to generate precipitate VII that contains factor XIII. Add an EDTA solution to precipitate VII and dialyze against a Tris-HCl buffer containing EDTA and sodium azide. After adjusting pH, remove precipitate VIII and have supernatant VIII undergo gel filtration to collect active fractions. Add ammonium sulfate to the fractions and collect precipitate IX containing factor XIII. Dissolve this precipitate IX in a Tris-HCl buffer containing EDTA, dialyze against the same buffer, and adjust pH to collect a precipitate that contains factor XIII in the form of euglobulin. Dissolve the euglobulin precipitate in an Nacl solution containing EDTA, and add aminoacetic acid and sucrose. Then add ammonium sulfate to generate precipitate X containing factor XIII, and dissolve this precipitate X in an Nacl solution containing EDTA, and dialyze against the same solution. Adjust the titer of factor XIII using an Nacl solution containing glucose and human serum albumin. Have this solution undergo sterile filtration, dispense into glass vials, and lyophilyze.

In addition to the above-mentioned fractionation method, factor XIII can also be manufactured by use of genetic engineering. Factor XIII preparations in accordance with this invention include all the factor XIII preparations manufactured by any possible method, including fractionation methods and genetic engineering methods.

Since factor XIII preparations manufactured by fractionation methods may possibly contain hepatitis virus, AIDS virus, etc., it is desired to inactivate these viruses by heat treatment or some other means. The heat treatment is performed as follows: dissolve the precipitate containing factor XIII in the form of euglobulin in an NaCl solution containing EDTA, and allow the solution to stand at approximately 60+ C. for 10 hours or so. Amino acids (e.g., glycine), hydrocarbonates, etc. can be used as stabilizers during this incubation.

A lyophilized factor XIII preparation can directly be used as an injection by just dissolving it in distilled water for injection (JP), etc. before use. The concentration of factor XIII in the injection should be about 250 units/4 ml. The injection can be given either intravenously or intramuscularly. No change has been reported to be induced by mixture with other agents. It is generally considered, however, that administration of factor XIII mixed with other agents should be avoided.

Most desirably, factor XIII should be administered by injection, but possible dosage forms include parenteral ones such as micro-capsules and implants, oral ones such as liquids, tablets and capsules, and suppositories.

DOSAGE AND TREATMENT PERIOD

The daily dosage necessary to sufficiently enhance factor XIII activity in patients with active-stage ulcerative colitis is approximately 5000 units or less. The optimum dose range is from 1500 to 3000 units daily.

Administration should be continued until the patient's symptoms virtually disappear, i.e., for 3 to 5 days in usual cases. In cases where symptoms recur, administration may be restarted at any time.

Example8 Factor XIII, dispensed into vials by 250 units each and lyophilized, was dissolved in 4 ml of distilled water for injection (JP) to make a factor XIII injection.

What is claimed is:

1. A process for the treatment of ulcerative colitis characterized by administering to a patient requiring such treatment a daily dosage level of from 1500 to about 5000 units of human blood coagulation factor XIII concentrate.

2. The process of claim 1 wherein said concentrate is obtained by fractionation of human blood plasma.

3. The process of claim 1 wherein said human blood coagulation factor XIII is administered as an injection at a concentration of about 250 units/4 ml of water.

4. The process of claim 1 wherein said human blood coagulation factor XIII is administered at a daily dosage level of from 1500 to 3000 units of concentrate.

* * * * *